US012690878B2

(12) United States Patent
Bloem et al.

(10) Patent No.: US 12,690,878 B2
(45) Date of Patent: Jul. 28, 2026

(54) KIDNEY STONE IDENTIFICATION SYSTEM

(71) Applicant: GYRUS ACMI, INC., Westborough, MA (US)

(72) Inventors: David Bloem, Maple Grove, MN (US); Charles A. Baker, Rogers, MN (US); Kurt G. Shelton, Bedford, MA (US)

(73) Assignee: Gyrus ACMI, Inc., Westborough, MA (US)

( * ) Notice: Subject to any disclaimer, the term of this patent is extended or adjusted under 35 U.S.C. 154(b) by 534 days.

(21) Appl. No.: 18/133,362

(22) Filed: Apr. 11, 2023

(65) Prior Publication Data

US 2023/0346400 A1 Nov. 2, 2023

Related U.S. Application Data

(60) Provisional application No. 63/363,839, filed on Apr. 29, 2022.

(51) Int. Cl.
 *A61B 10/02* (2006.01)
 *A61B 17/22* (2006.01)
 (Continued)

(52) U.S. Cl.
 CPC ....... *A61B 17/22004* (2013.01); *G06N 20/00* (2019.01); *A61B 10/0096* (2013.01);
 (Continued)

(58) Field of Classification Search
 None
 See application file for complete search history.

(56) References Cited

U.S. PATENT DOCUMENTS

| | | | | |
|---|---|---|---|---|
| 5,536,242 A | * | 7/1996 | Willard | A61M 1/77 604/35 |
| 2007/0225781 A1 | * | 9/2007 | Saadat | A61F 7/12 607/105 |

(Continued)

FOREIGN PATENT DOCUMENTS

| | | |
|---|---|---|
| CN | 116965886 | 10/2023 |
| DE | 102023109521 | 11/2023 |

(Continued)

OTHER PUBLICATIONS

"Japanese Application Serial No. 2023-075040, Notification of Reasons for Rejection mailed Feb. 19, 2024", W English Translation, 17 pgs.

(Continued)

*Primary Examiner* — Aurelie H Tu
(74) *Attorney, Agent, or Firm* — Schwegman Lundberg & Woessner. P.A.

(57) ABSTRACT

System and techniques for target identification system are described herein. In an example, a system can include a medical instrument for ablating a target and a mechanism for removing the ablated target from an anatomic site into an evacuation path. The evacuation path can include a measurement chamber. The system can also include a turbulence-generation system that can generate turbulence in the measurement chamber. The system can also include a target-identification system that can determine a characteristic of at least a portion of the ablated target in the measurement chamber.

21 Claims, 11 Drawing Sheets

(51) Int. Cl.

| | |
|---|---|
| *A61B 17/32* | (2006.01) |
| *A61B 18/14* | (2006.01) |
| *G06N 20/00* | (2019.01) |
| *A61B 10/00* | (2006.01) |
| *A61B 17/00* | (2006.01) |

(52) U.S. Cl.

CPC .............. *A61B 2017/00061* (2013.01); *A61B 2017/22005* (2013.01); *A61B 2017/22079* (2013.01)

(56) References Cited

U.S. PATENT DOCUMENTS

| | | | | |
|---|---|---|---|---|
| 2008/0200828 | A1* | 8/2008 | Abboud | A61B 5/0537 600/547 |
| 2009/0062872 | A1* | 3/2009 | Chin | A61B 1/00082 606/86 R |
| 2013/0204134 | A1* | 8/2013 | Harks | A61B 8/12 600/439 |
| 2015/0011855 | A1* | 1/2015 | Burnett | A61M 5/14276 600/365 |
| 2016/0242661 | A1* | 8/2016 | Fischell | A61B 5/24 |
| 2022/0005198 | A1* | 1/2022 | Goldberg | A61B 5/364 |
| 2022/0061827 | A1 | 3/2022 | Schmitt et al. | |

FOREIGN PATENT DOCUMENTS

| | | |
|---|---|---|
| JP | 2009536261 | 10/2009 |
| WO | 2008011213 | 1/2008 |
| WO | 2022047152 | 3/2022 |

OTHER PUBLICATIONS

"Japanese Application Serial No. 2023-075040, Response filed May 17, 2024 to Notification of Reasons for Rejection mailed Feb. 19, 2024", W English Claims, 14 pgs.

"Japanese Application Serial No. 2023-075040, Final Notification of Reasons for Rejection mailed Jul. 29, 2024", W English Translation, 6 pgs.

"Japanese Application Serial No. 2023-075040, Response filed Oct. 29, 2024 to Final Notification of Reasons for Rejection mailed Jul. 29, 2024", W English Claims, 11 pgs.

* cited by examiner

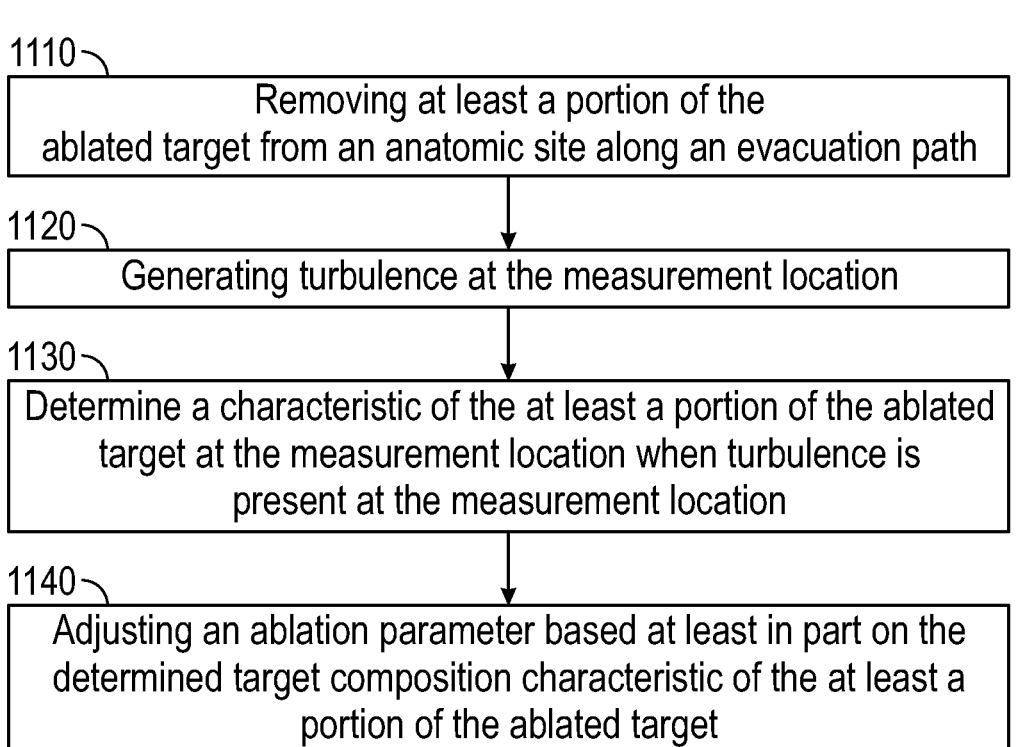

1100

1110 ─

Removing at least a portion of the
ablated target from an anatomic site along an evacuation path

1120 ─

Generating turbulence at the measurement location

1130 ─

Determine a characteristic of the at least a portion of the ablated
target at the measurement location when turbulence is
present at the measurement location

1140 ─

Adjusting an ablation parameter based at least in part on the
determined target composition characteristic of the at least a
portion of the ablated target

FIG. 11

KIDNEY STONE IDENTIFICATION SYSTEM

CLAIM OF PRIORITY

This patent application claims the benefit of priority to David Bloem U.S. Patent Application Ser. No. 63/363,839, entitled "KIDNEY STONE IDENTIFICATION SYSTEM," filed on Apr. 29, 2022, which is hereby incorporated by reference herein in its entirety.

TECHNICAL FIELD

The present disclosure relates to an identification system and, more specifically, an identification system for an anatomical target.

BACKGROUND

It can be difficult for medical professionals to accurately distinguish between the different types of targets encountered during medical procedures. For example, it can be difficult for medical professionals to distinguish between the different kidney stone types accurately. Also, the process of kidney stone identification can be difficult and time-consuming. Medical professionals can identify kidney stones through various diagnostic tests such as ultrasound, CT scans, X-rays, and blood and urine tests.

The ability to accurately identify kidney stones can be important for patient care. For example, accurately identifying kidney stones can help clinicians select the most appropriate treatment option. Additionally, accurate identification of kidney stones can help clinicians better understand the underlying cause of the kidney stone and take steps to prevent it from recurring.

BRIEF DESCRIPTION OF THE DRAWINGS

Various examples are illustrated in the figures of the accompanying drawings. Such examples are demonstrative and not intended to be exhaustive or exclusive embodiments of the present subject matter.

FIG. 11 is a schematic diagram of an example of a method of using a system for identifying targets.

DETAILED DESCRIPTION

This document describes, among other things, a system that can include a medical instrument for ablating a target and a mechanism for removing the ablated target from an anatomic site into an evacuation path. The evacuation path can include a measurement chamber. The system can also include a turbulence-generation system that can generate turbulence in the measurement chamber. The system can also include a target-identification system that can determine a characteristic of at least a portion of the ablated target in the measurement chamber.

Various pulse, wave, or other energy generating sources can be used to ablate a target within an anatomical region of a patient. For example, a ShockPulse SE Ultrasonic generator can be used for a Percutaneous Nephrolithotomy (PCNL) procedure to remove large kidney stones (e.g., those with a diameter over 2 cm). Common types of kidney stones can include calcium oxalate monohydrate, cystine, and uric acid. Each of these different types of kidney stones can be identified by comparing their respective color, shape, size, and roughness.

A hollow ultrasonic probe can be included in or coupled to the ultrasonic generator can act as a jackhammer to fragment large stones into smaller pieces. One or mor irrigation sources and suction sources can be used to aspirate those small pieces and direct them into a collection device. These small pieces or fragments of stones can be collected in a catch basin that can be attached to the aspiration tubing, such as at a location away from the transducer of the ultrasonic generator. Fragments from the catch bin can be transported for lab analysis to determine the chemistry and composition of the targeted stone.

The present inventors have identified at least two problems with such procedures. First, stone fragments can become clogged in the tubing between the ultrasonic generator and the tubing used to direct the small pieces and fragments of the stone to the collection device. Second, sending the captured stone fragments to the lab for identification via assay is a post-procedure operation that can be expensive and time-consuming. Therefore, the present inventors have developed a kidney stone identification system that can include a removable collection device, or multiple removable collection devices, and can include in-line and offline analysis of the fragmented kidney stones collected within a collection device. To improve the speed and accuracy of the analysis of the fragmented portions of a stone, convolutional neural networks, machine learning, or algorithmic techniques can be implemented by the kidney stone identification system. The kidney stone identification system will be discussed herein with reference to FIGS. 1-12.

Figure 1:
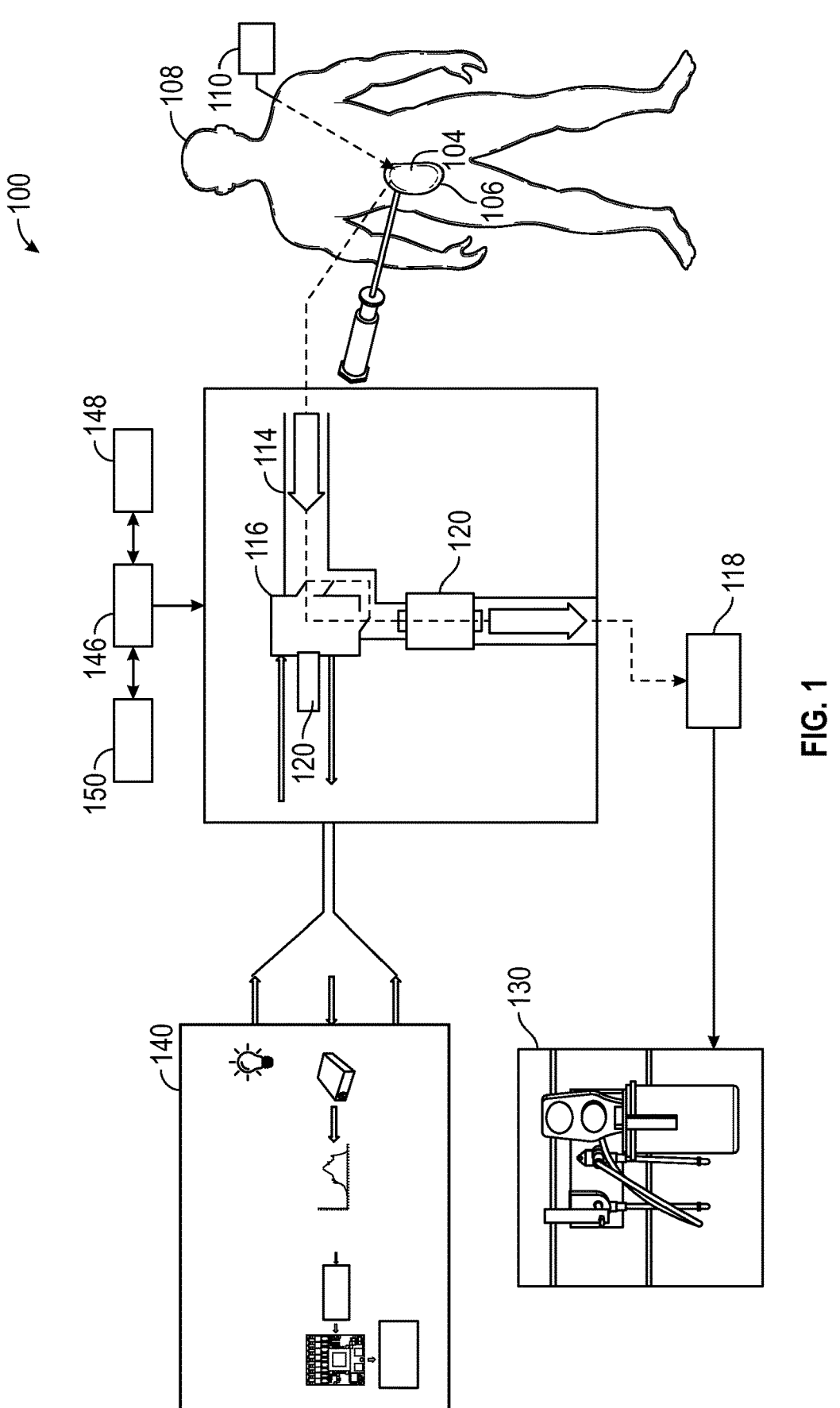
FIG. 1 is a schematic diagram of an example system for ablating and analyzing a target within an anatomic site.

FIG. 1 is a schematic diagram of an example of a system 100 for ablating and analyzing a target 104 within an anatomic site 106. The system 100 can include a medical ablation instrument 102, a turbulator 120, a removable trap filter 122, a suction source 130, a target composition characterization system 140, and a controller 146.

The medical ablation instrument 102 can be configured to ablate a portion of a target 104 located at an anatomic site 106 within a patient 108. For example, the medical ablation instrument 102 can include an ultrasonic lithotripter probe or a fluoroscopic lithotripter probe or any other probe, device, or medical instrument that can be used to ablate the target 104, or at least a portion of the target 104, from the patient 108, or the like. The target 104 can include a kidney stone, growth, cyst, or any other abnormality or anomaly within the patient 108. The medical ablation instrument 102 can define an evacuation path 114 therewithin.

As shown in FIG. 1, an irrigation source 110 can be used during the ablation procedure to provide liquid to the anatomic site 106 during the ablation of the target 104. The irrigation source 110 can provide water, saline, other biocompatible fluid, or the like to the anatomic site 106 within the patient 108. The fluid from the irrigation source 110 can carry an ablated portion of the target 104 into the evacuation path 114. Thus, a mixture of the liquid from the irrigation source 110 and the ablated portion of fragments of the target 104 can flow through the evacuation path 114.

The evacuation path 114 can include a measurement location 116. The measurement location 116 can collect the ablated portion of the target 104. The liquid from the irrigation source 110 can continue through the measurement location 116, which can leave behind the fragments of the target 104 in the measurement location 116. The fragments of the target 104 can be collected for in-line analysis, captured to be removed from the evacuation path 114 for offline analysis, or for post-procedure analysis to confirm any intraprocedural findings. The measurement location 116 can include a volume indicator, which can help to quickly measure the volume of the fragments captured within the measurement location 116. In examples, the mixture of the liquid from the irrigation source 110 and the fragments of the target 104 can be captured in the measurement location 116. The mixture can be collected for in-line analysis, captured to be removed from the evacuation path 114 for offline analysis, or for post-procedure analysis to confirm any intraprocedural findings. The measurement location 116 can include a volume indicator, which can help to quickly measure the volume of the mixture captured within the measurement location 116.

The turbulator 120 can be connected to the system 100 via the measurement location 116 of the evacuation path 114. The turbulator 120 can be configured to generate turbulence of the mixture within the measurement location 116 or to agitate the fragments of the target 104 captured within the measurement location 116. The turbulator 120 can include a static turbulator, for example, a ball turbulator, spring turbulator, twisted tape turbulator, matrix turbulator, or any turbulator that can generate turbulence, or near turbulence disturbances, in the mixture of the liquid from the irrigation source 110 and the ablated portion of the target 104 within the measurement location 116 of the evacuation path 114. The static turbulator need not move. For example, the mixture of the liquid from the irrigation source 110 and the ablated portion of the target 104 can be pumped through the turbulator 120 as the mixture flows into the measurement location 116 such that the mixture within the measurement location 116 can include turbulence. The turbulator 120 can be a dynamic (e.g., moving) turbulator that can generate turbulence of the mixture within the measurement location 116 or agitate the fragments of the target 104 captured within the measurement location 116. The turbulator 120 can also be an active turbulator that includes an ultrasound or other acoustic generator to generate cavitation in the fluid, thereby creating turbulence and agitation in the mixture.

The removable trap filter 122 can be configured to store the ablated portions of the target 104. As such, the removable trap filter 122 can be configured to catch the fragments of the ablated target 104 and to permit the liquid from the irrigation source 110 to pass therethrough. The removable trap filter 122 can include one or more volume indicators, which can help quickly measure a volume of the fragments of the target captured within the removable trap filter 122.

The removable trap filter 122 can located within the evacuation path 114. The removable trap filter 122 can be located downstream of the measurement location 116. The removable trap filter 122 can be located between the medical ablation instrument 102 and the measurement location 116. A first removable trap filter 122 can be located between the medical ablation instrument 102 and the measurement location 116 and a second of the removable trap filter 122 can be located downstream of the measurement location 116. When the end user removes the removable trap filter 122, the removable trap filter 122 can enable off-line testing or analysis of the ablated target 104, which can help confirm the findings of the in-line analysis or provide further information about the ablated target 104. An example of the removable trap filter 122 will be discussed with reference to FIG. 6.

The suction source 130 can be fluidically connected to the evacuation path 114 such as to draw the mixture of the liquid from the irrigation source 110 and the ablated portion of the target 104 through the evacuation path 114. The suction source 130 can include a hospital wall vacuum, a mobile pump within the room of the medical procedure, or any other pump or vacuum that can provide a suction source that can draw the mixture through the evacuation path 114. The evacuation path 114 can also include an irrigation reservoir 118 that can be fluidically connected between the measurement location 116 and the suction source 130 such as to recoup, store, or divert some of the liquid from the irrigation source 110 after it has been drawn through the evacuation path 114 via the suction source 130.

The target composition characterization system 140 can be operatively coupled to the measurement location 116 of the evacuation path 114. The target composition characterization system 140 can be configured to determine a composition characteristic of at least a portion of the ablated target 104 along the evacuation path 114 within the system 100. The target composition characterization system 140 can include an ultrasonic generator, which can include a stone composition analyzer. The target composition characterization system 140 can be coupled to the removable trap filter 122, or any other portions of the evacuation path 114 to analyze the fragments of the target 104 therewithin. The target composition characterization system 140 can also include an offline device that is not coupled to the measurement location 116, which can receive one or more of the removable trap filter 122 to analyze the fragments of the target 104 captured therewithin.

The controller 146 can be configured to control one or more parameters of the system 100. For example, the system 100 can control an amount of liquid from the irrigation source 110, agitation from the turbulator 120, suction from the suction source 130, any other parameter of the system 100, or the like. The controller 146 can be coupled to a memory 148. The memory 148 can maintain instructions, algorithms, programs, or the like that can instruct the controller 146 to control or operate the other components of the system 100. The memory 148 will be discussed in more detail herein. The controller 146 can be connected to a convolutional neural network (CNN) or another cloud network (e.g., network 150). The CNN and the network 150 can offload some of the computing of the controller 146 to provide faster, more accurate results. Moreover, the CNN and the network 150 can transmit one or more updates based on the results of other devices or systems connected to the network 150 or the cloud system. The network 150 and the cloud system will be discussed in more detail herein.

Figure 2:
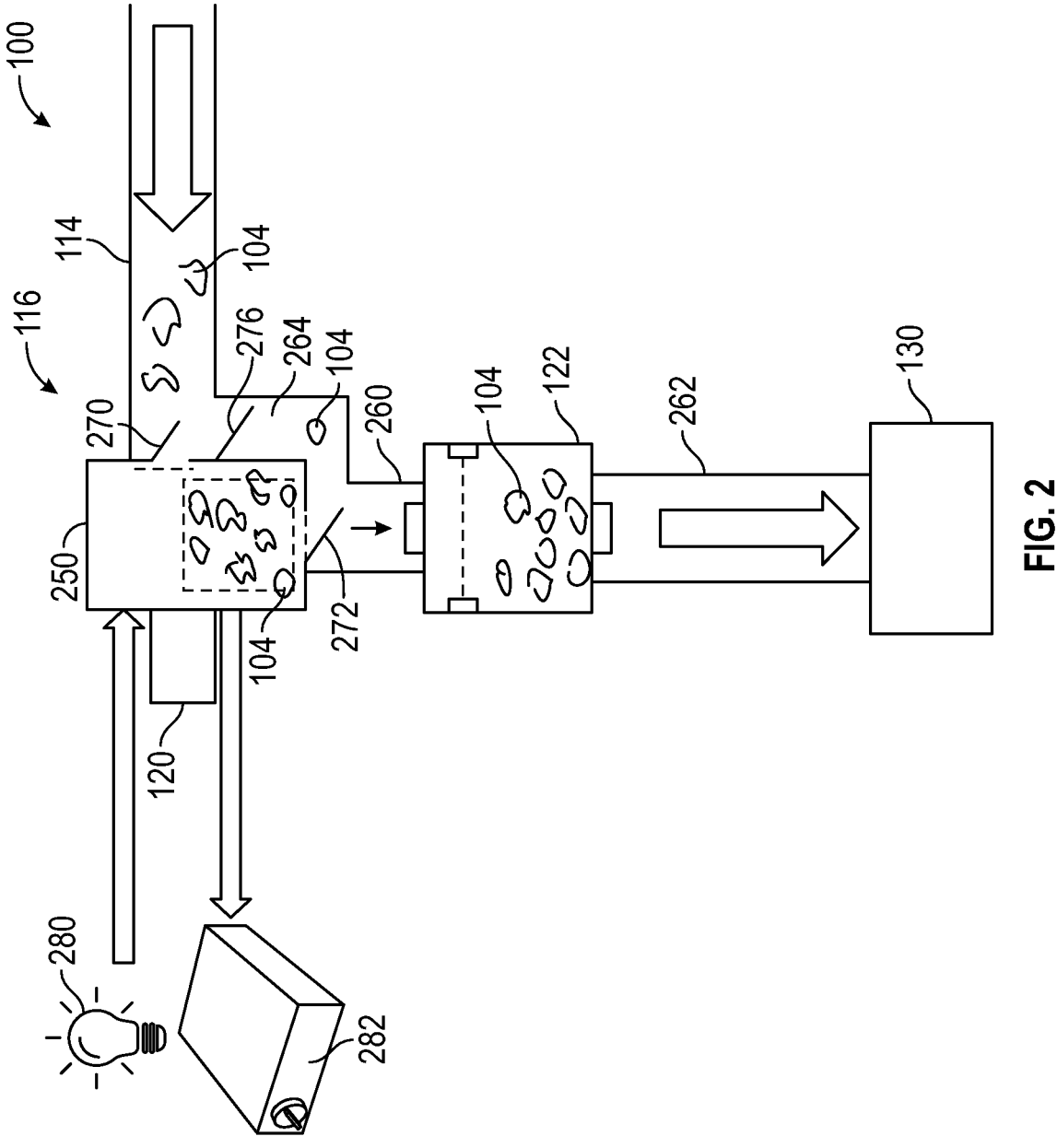
FIG. 2 illustrates a portion of an example of a system that can be used to analyze ablated portions of a target within an anatomic site.

FIG. 2 illustrates a portion of the system 100 that can be used to help analyze ablated portions of the target 104 (FIG. 1). As discussed above, the system 100 can include a measurement location 116 and a removable trap filter 122 located downstream from the measurement location 116. The system 100 can also include suction line 260 and suction line 262 that can extend between the patient 108 (FIG. 1) and the suction source 130. The suction line 260 can be part of an endoscope that is inserted into a patient during a target ablation procedure. The suction source 130 can pull debris, such as the target 104 dislodged during an ablation procedure, from the patient. During an ablation procedure, kidney stones within a patient can be subjected to ultrasonic or other acoustic wave energy or a laser, thereby dislodging target 104 from kidney stones or other targets in the patient.

The measurement location 116 can include a measurement chamber 250. The measurement chamber 250 can include an inlet valve 270 and an outlet valve 272. The system 100 can also include a bypass valve 276. The inlet valve 270 and the outlet valve 272 can be operable to control the flow of the mixture of the liquid from the irrigation source 110 and the fragments of the target 104 into the measurement chamber 250 and the flow of the mixture of the liquid from the irrigation source 110 and the fragments of the target 104 out of the measurement chamber 250, respectively. The inlet valve 270, the outlet valve 272, and the bypass valve 276 will be discussed in more detail with reference to FIGS. 5A-5C.

When the fragments of the target 104 are disposed within the measurement location 116, or more specifically, within the measurement chamber 250, the fragments of the target 104 can be subjected to a spectroscopy procedure to determine a type of kidney stone or other anatomical structures from which the fragments of the target 104 were ablated. More specifically, the target 104 within the measurement location 116 or the measurement chamber 250 can be exposed to light from a light source 280, and using various spectrometry techniques, a spectrometer 282 can generate a signal that permits the target composition characterization system 140 (FIG. 1) to identify the composition of the target 104. With this information, an ablation technique can be determined that will provide the most effective ablation of the target 104 within the patient 108.

The kidney stones, or other anatomical structures, from which the fragments of the target 104 are dislodged can be heterogeneous. Thus, multiple measurements can be taken to get a more accurate measure of the composition of the target 104 and the kidney stones, or other anatomical structures, within the patient 108. The measurement chamber 250 can be configured to agitate the target 104 within the measurement chamber 250 to allow for more accurate measurements. For example, the turbulator 120 can be configured to agitate the target 104 within the measurement chamber 250 to allow for more accurate measurements by the system 100.

The signal from the spectrometer 282 and the target composition characterization system 140, or another controller of the system (e.g., the controller 146) can also be used to estimate the mass of the fragments of the target 104 within the measurement location 116 or the measurement chamber 250. As such, the system (e.g., the system 100) can include another sensor, for example, a particle size sensor, image sensor, optical sensor, electrostatic, capacitive, mechanical, or any other sensor that can determine the size of the fragments of the target 104, which can be used to count the number of particles or fragments of the target 104 along the evacuation path 114 over a period of time. Here, the system 100 can use the detected amount of particles within the evacuation path 114 over a period of time to determine an ablation rate of the target 104. The controller, CNN, or any other component of the system 100 can then provide feedback directly to the system 100, or to the medical professional to improve the ablation of the target 104. For example, the controller, CNN, or other components of the system 100 can indicate adjustments to the power of the energy source used for ablation, the pressure used during the ablation, or an amount or speed of the liquid used during the ablation to improve the ablation results of the target 104. Moreover, the controller, CNN, or other components of the system 100 can estimate the time needed to complete the procedure based on the initial volume of the target 104 and the ablation rate found during the procedure.

Figures 3, 4:
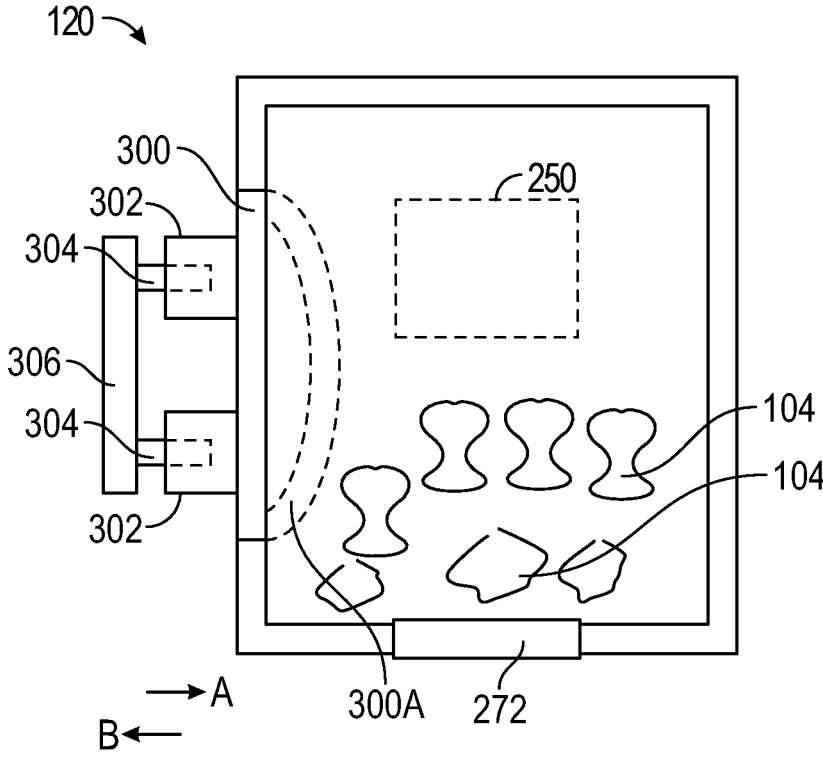
FIG. 3 illustrates an example of a measurement chamber of a system, including an example of a turbulator.
FIG. 4 illustrates fragments of the target dislodged from a patient.

FIG. 3 illustrates an example of the measurement chamber 250 of the system 100 including an example of the turbulator 120. In FIG. 3, the outlet valve 272 is shown in a closed configuration. The turbulator 120 can be connected to the measurement chamber 250. The turbulator 120 can include a flexible member 300 in contact with pistons 302 of an agitating device comprising cylinders 304 on which the pistons 302 move along direction A and direction B. The pistons 302 can be a part of a solenoid 306. The solenoid 306 can cause movement of the pistons 302 along the direction A and the direction B. When the pistons 302 move along the direction A, the pistons can contact the flexible member 300, thereby causing the flexible member 300 to flex within the measurement chamber 250, as shown at 300A. The solenoid 306 can cause the pistons to move along the directions A and B at a rate that causes the flexible member 300 to flex into and out of the configuration shown at 300A. As the flexible member 300 can flex into and out of the configuration shown at 300A, and the target 104 can be agitated within the measurement chamber 250.

FIG. 4 illustrates an illustrative example of a fragment of the target 104 dislodged from a patient 108 (FIG. 1). The fragments of the target 104 can include sides 400-406. During agitation of the fragments of the target 104, the fragments of the target 104 can be exposed to light from the light source 280. As the fragments of the target 104 are exposed to light from the light source 280, the spectrometer 282 can take measurements of the illumination response energy emitted from the target 104 and the sides 400-406 to allow for more accurate measurements of the target 104. As the fragments of the target 104 are agitated, the fragments of the target 104 can move around in different directions, thereby exposing each of the sides 400-406 to light emitted from the light source 280. As such, the spectrometer 282 can take measurements of the energy radiated from the fragments of the target 104 and any combination of the sides 400-406 as the fragments of the target 104 are agitated. The measurements taken by the spectrometer 282 can be indicative of a composition of the fragments of the target 104. The agitation and turbulence generated can help take measurements around the fragments of the target 104, which can help capture an average reading to determine one or more characteristics of the fragments of the target 104.

In addition to agitating the fragments of the target 104 via the pistons 302 and the solenoid 306, the suction source 130 can draw the liquid from the irrigation source 110 (FIG. 1) and the fragments of the target 104 through the suction lines 260 (FIG. 2) and the bypass line 264 (FIG. 2). As the liquid from the irrigation source 110 and the fragments of the target 104 passes the inlet valve 270, with the inlet valve 270 in the open position, a pressure differential can be created between the suction line 260 and the measurement chamber 250. The pressure differential between the suction line 260 and the measurement chamber 250 can generate movement of the fragments of the target 104 within the measurement chamber 250 and further agitate the fragments of the target 104 within measurement chamber 250.

Returning attention to FIG. 2, as noted above, the system 100 can also include the removable trap filter 122. The removable trap filter 122 can capture the fragments of the target 104 that travel through the bypass line 264 (FIG. 2). In addition, after measurements of the fragments of the target 104 are conducted within the measurement chamber 250, the outlet valve 272 can be opened. When the outlet valve 272 is opened, the fragments from the target 104 can exit from measurement chamber 250 and enter into the removable trap filter 122.

Figures 5A, 5B, 5C:
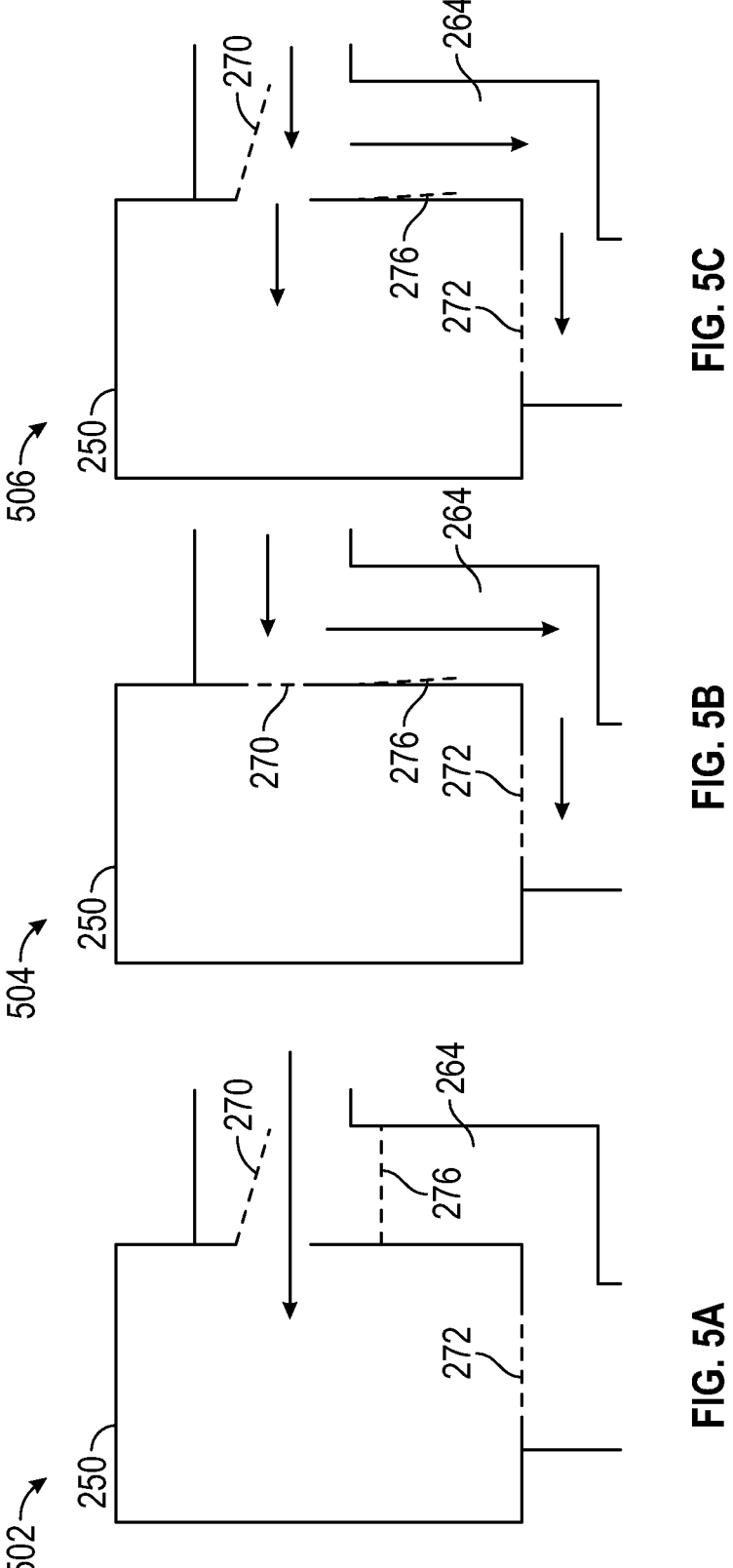
FIGS. 5A-5C illustrate an example of a measurement chamber operating in three different operational modes.

FIGS. 5A-5C illustrate an example of the measurement chamber of a system for analyzing kidney stone fragments in three different operational modes. The inlet valve 270, the outlet valve 272, and the bypass valve 276 can operate between an open configuration and a closed configuration. Thus, the inlet valve 270, the outlet valve 272, and the bypass valve 276 can be actuated, for example by a controller (e.g., the controller 146 or another controller of the system 100 (FIG. 1)), to operate the system 100 between a first operating mode 502, a second operating mode 504, and a third operating mode 506.

In the first operating mode 502, the inlet valve 270 can be in an open position, the outlet valve 272 can be in a closed position, and the bypass valve 276 can be in a closed position. In the first operating mode 502, the inlet valve 270, the outlet valve 272, and the bypass valve 276 can direct the mixture of liquid from the irrigation source 110 and the fragments from the target 104 into the measurement chamber 250. The first operating mode 502 can be used to trap fragments of the target 104 within the measurement chamber 250, which can permit the target composition characterization system 140 to analyze the fragments of the target 104 during the ablation procedure.

In the second operating mode 504, the inlet valve 270 can be in a closed position, the outlet valve 272 can be in a closed position, and the bypass valve 276 can be in an open position. In the second operating mode 504, the liquid from the irrigation source 110 and the fragments of the target 104 can flow through the bypass line 264 and bypass the measurement chamber 250. The second operating mode 504 can be used to fill the removable trap filter 122 quickly or to purge the system 100 of debris found within the evacuation path 114.

In the third operating mode 506, the inlet valve 270 can be in an open position, the outlet valve 272 can be in a closed position, and the bypass valve 276 can be in an open position. In the third operating mode 506, the mixture of the liquid from the irrigation source 110 and the fragments of the target 104 can both flow through the measurement chamber 250 and the bypass line 264. In the third operating mode 506, the system 100 can analyze the fragments of the target 104 within the measurement chamber 250 while simultaneously collecting the fragments of the target 104 within the removable trap filter 122. As such, the system 100 can analyze the fragments of the target 104 that are within the measurement chamber 250 while other fragments of the target 104 are collected within the removable trap filter 122. So, in the third operating mode 506, the system 100 can include in-line readings of the fragments of the target 104 while also filling the removable trap filter 122 more quickly than when the system 100 is in the first operating mode 502, such that the off-line analysis can be completed closer in time to the in-line analysis than when the system 100 is in the first operating mode 502.

Additional valves can be included to direct the mixture of the liquid from the irrigation source 110 and the fragments of the target 104 through any additional measurement locations or removable filters throughout the evacuation path 114. For example, a valve can be located in the evacuation path 114 nearest the patient to direct the first of the mixture into a removable trap filter or a measurement site to take initial measurements or readings of the fragments of the target 104. The valves of the system 100 can be opened or closed based on input from the medical professional operating the system. In another example, the valves can be operated based on one or more of the controllers of the system, the convolutional neural network, or the network, to alter the flow of the mixture through the evacuation path 114, which can help the system 100 or the medical professional verify or check any of the readings found during the medical procedure.

Figure 6:
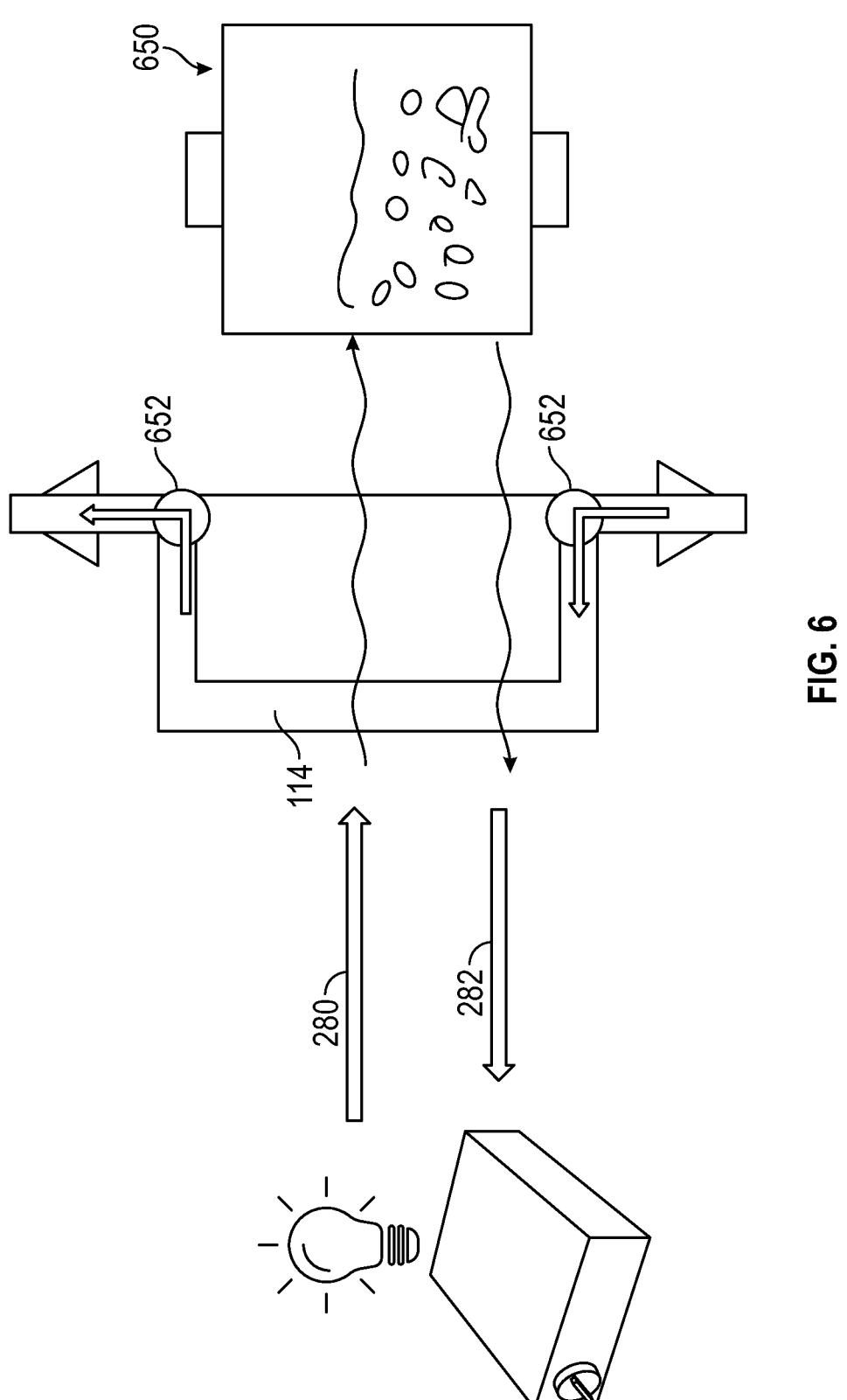
FIG. 6 illustrates an example of a measurement chamber.

FIG. 6 illustrates an alternative example of a measurement chamber 650. The measurement chamber 650 can be removably attached from the evacuation path 114 such that the measurement chamber 650 can be removed during the operation of the system. For example, the evacuation path 114 can include one or more valves 652 that can expand when the measurement chamber 650 is removed to direct liquid and fragments through the evacuation path 114. The valves on the evacuation path 114 can be engaged by the measurement chamber 650 as the measurement chamber 650 is installed within the evacuation path 114 to create openings in the evacuation path 114 and direct the liquid and the fragments into the measurement chamber 650.

The one or more valves 652 can hold the measurement chamber 650 within the evacuation path 114 when the measurement chamber 650 is installed in the evacuation path 114. In examples, the measurement chamber 650 can be threadedly engaged with components of the evacuation path 114 (e.g., the one or more valves 652) to connect or disconnect the measurement chamber 650 from the evacuation path 114.

Thus, the measurement chamber 650 shown in FIG. 6 allows the fragments of the target to be analyzed in-line during the procedure in which the system is ablating the target. For example, a reference light source output 280 and a spectrometer 282 can detect one or more characteristics of the fragments of the targets removed from the patients. Additionally, the measurement chamber 650 can be removed for offline analysis while the system 100 (FIG. 1) continues to be used to ablate the target. For example, when the measurement chamber 650 is removed and the system is still operating, the fragments of the target can be collected in a removable trap filter (e.g., the removable trap filter 122 (FIG. 1)).

Figure 7:
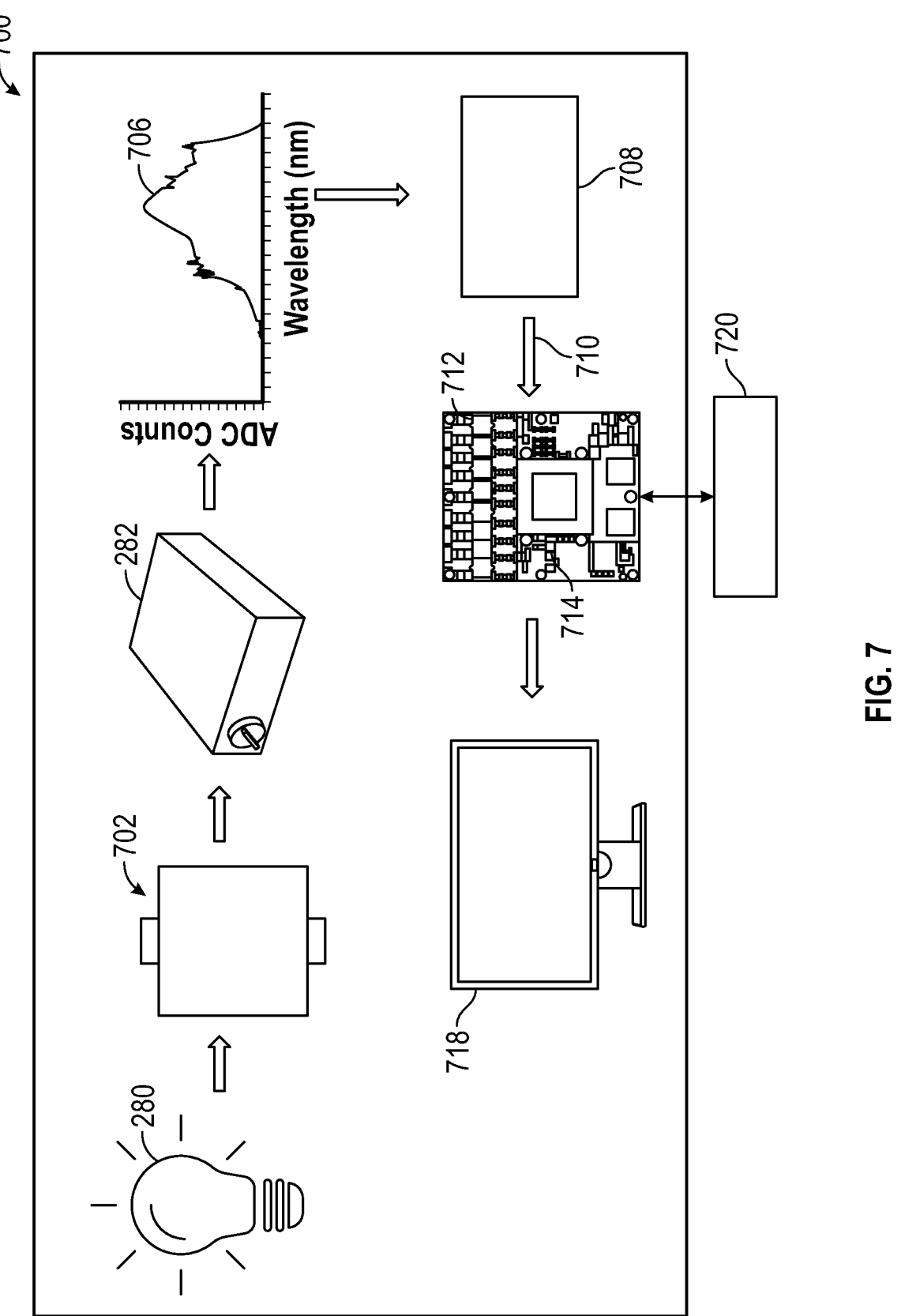
FIG. 7 is a schematic diagram of an example of a target composition analyzer.

FIG. 7 is a schematic diagram of an example of a target composition analyzer 700. As discussed above, the target composition analyzer 700 can be used to characterize the fragments of the target. The target composition analyzer 700 can be used to analyze a sample cartridge 702 (e.g., the removable trap filter 122) offline. So, the sample cartridge 702 can be removed from the evacuation path 114 (FIG. 1) and put into the target composition analyzer 700.

The light source 280 can transmit light across the sample cartridge 702, and the spectrometer 282 can receive the light transmitted across the sample cartridge 702. The spectrometer 282 can generate a signal indicative of a spectral response 706 generated by the fragments of the target 104.

The signal indicative of the spectral response 706 can be transmitted to a feature extractor 708. The feature extractor 708 can extract features from the spectral response 706. For example, the feature extractor 708 can determine a maximum or minimum value, a range, an average, a median, or any other characteristic of the data from the spectral response 706. The feature extractor 708 can also normalize the data into a form or format used by other components of the target composition analyzer 700 or the system 100 (FIG. 1). The feature extractor 708 can transmit the found features as feature output 710.

The target composition analyzer 700 can include a machine learning classifier 712. The machine learning classifier 712 can be a controller (e.g., the controller 146 (FIG. 1)), which can control one or more characteristics of the system (e.g., the system 100 (FIG. 1)). The controller can also analyze the fragments of the target 104 (FIG. 1) and provide an identification of the fragments. A machine learning classifier 712 can receive the spectral response 706 and the feature output 710. The machine learning classifier 712 can be used to classify the fragments of the target by comparing the spectral response 706 and the feature output 710 to reference data that can be used to teach or train the machine learning classifier 712. The operations and functions of the machine learning classifier 712 will be discussed in more detail with reference to FIG. 9 below.

The machine learning classifier 712 can include processing circuitry 714, which instructions stored on the memory (e.g., the memory 148 (FIG. 1)) can cause the machine learning classifier 712 to complete various tasks. For example, the processing circuitry 714 (or any other processing circuitry of any other controller discussed herein) of the machine learning classifier 712 can generate a stone identification output 716. The controller can receive the response signal from the spectrometer. For example, the machine learning classifier 712 can receive the feature output 710 from the feature extractor 708. The controller can analyze the response signal to determine the composition characteristic of the at least a portion of the ablated target. For example, the machine learning classifier 712 can compare the feature output 710 to at least one criterion. The controller can generate an output based on the comparison. For example, the processing circuitry 714 of the machine learning classifier 712 can generate a stone identification output 716 based on the comparison of the feature output 710 from the feature extractor 708 and at least one criterion.

The stone identification output 716 can include one or more identifiers or classifications of the fragments of the targets. For example, the stone identification output 716 can include calcium oxalate monohydrate, cystine, uric acid, or any combination thereof. The stone identification output 716 can also include a confidence score, which can relate to an accuracy estimate of the found results. The stone identification output 716 can be displayed on the target composition analyzer 700, transmitted back to a generator (e.g., the medical ablation instrument 102 from FIG. 1), or transmitted to an electronic health record system, which can store the stone identification output 716 into the health records of the patient.

The stone identification output 716 can be transmitted by the machine learning classifier 712 to a display 718. As discussed above, the display 718 can be on the generator or a part of the electronic health system. In another example, the display 718 can be a standalone display that can be installed within, or near such that the display 718 can be viewed from within, the room where the medical procedure is being performed.

In another example, the processing circuitry 714 (or any other processing circuitry described herein) can cause the machine learning classifier 712 (or any other controller described herein) to adjust a parameter associated with the medical target ablation instrument 102 based at least in part on the stone identification output 716 of the at least a portion of the ablated target. For example, in response to the stone identification output 716, the target composition analyzer 700 can transmit a signal to a system (e.g., system 100 from FIG. 1) to influence a selection of the ultrasonic probe (e.g., the medical ablation instrument 102 (FIG. 1)), control a power level, power efficiency, or a gain of the probe, or suggest a technique for ablation of the target to the health care provider. The target composition analyzer 700 can be configured such that the stone identification output 716 can maximize the sensitivity and specificity across all stone types while minimizing the occurrence of a not a stone (NAS) result.

The processing circuitry 714 of the machine learning classifier 712 or the processing circuitry of another controller (e.g., the controller 146 (FIG. 1)) can cause the controller to adjust a parameter associated with the medical target ablation instrument 102 based at least in part on the stone identification output 716 of the at least a portion of the ablated target. For example, the controller can receive an inflow rate indicative of a fluid flow (e.g., fluid from the 110 FIG. 1) going into a measurement chamber (e.g., the measurement location 116 (FIG. 1) along the evacuation path 114. The controller can also receive an outflow rate indicative of a fluid flow leaving the measurement chamber. The controller can then establish or adjust the inflow rate or the outflow rate to at least one of establish, adjust, or maintain a target turbulence level using the turbulator 120.

As shown in FIG. 7, a convolutional neural network 720 can be connected to the processing circuitry 714 of the machine learning classifier 712. The controller circuitry 714 can configure the machine learning classifier 712 to transmit a signal from the spectrometer to the convolutional neural network 720. For example, the processing circuitry 714 can transmit the spectral response 706, the feature output 710 from the feature extractor 708, or the stone identification output 716 to the convolutional neural network 720.

The convolutional neural network 720 can analyze or run test operations using the information transmitted thereto from the machine learning classifier 712 and can update instructions (e.g., algorithms) to improve the results of the analysis of the machine learning classifier 712, which can be transmitted back to the machine learning classifier 712. So, the machine learning classifier 712 can receive one or more updated instructions based on an output of the convolutional neural network 720.

Figure 8:
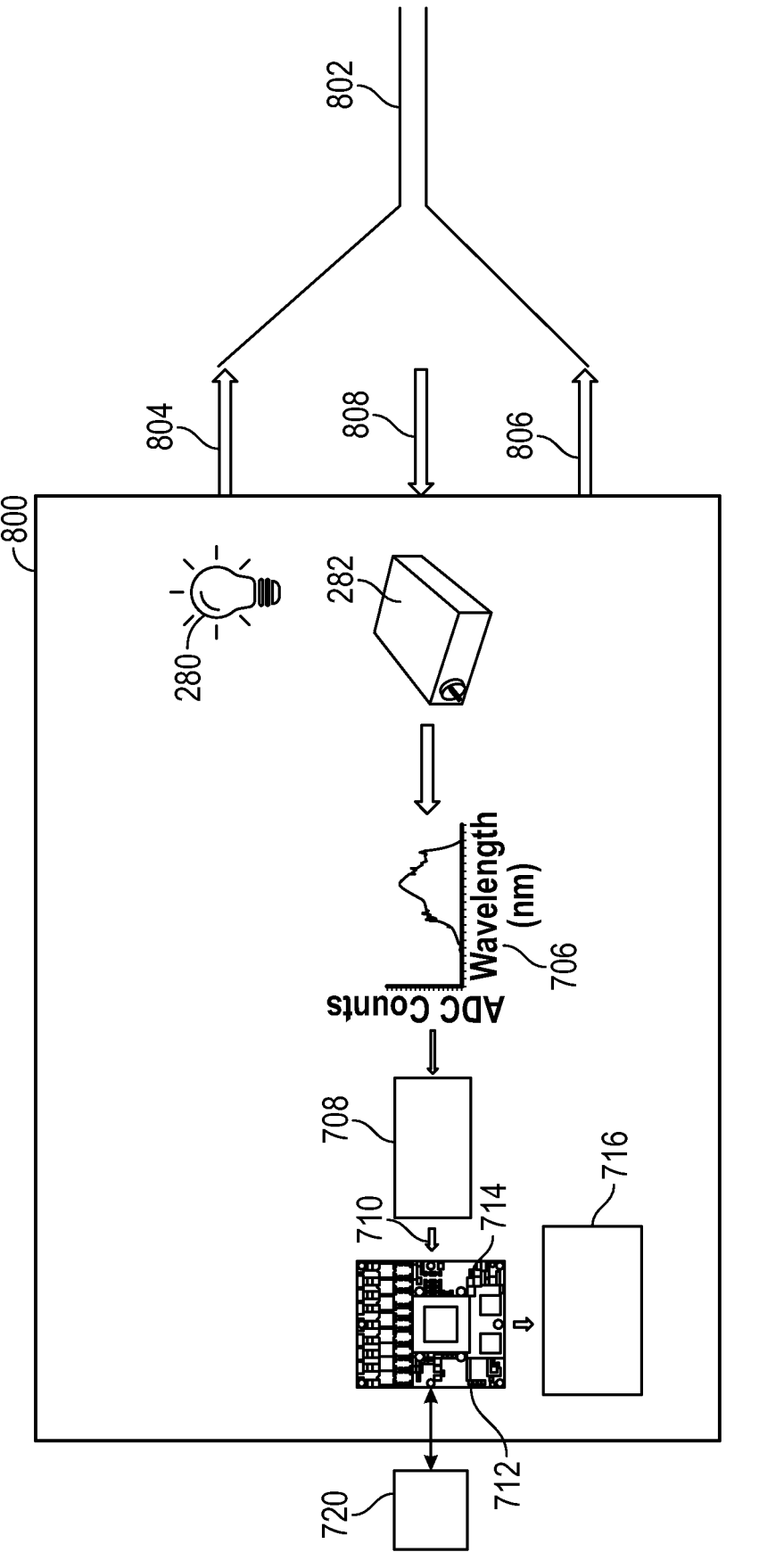
FIG. 8 is a schematic diagram of an example of a target composition analyzer.

FIG. 8 is a schematic diagram of an example of a target composition analyzer 800. The target composition analyzer 800 can be used to characterize the fragments of the target. The target composition analyzer 800 can be used to measure the fragments of the target 104 (FIG. 1) within the evacuation path 114, for example, within the measurement location 116, the measurement chamber 250 or the measurement chamber 650. For example, the target composition analyzer 800 can be used on a system that utilizes in-line identification of fragments of the target.

As shown in FIG. 8, a transducer cable 802 can be connected between the target composition analyzer 800 and one or more components of a system (e.g., the system 100

(FIG. 1)). The transducer cable 802 can include ultrasonic output drive lines 804, white source output fiber optic cables 806, and spectrometer input cables 808 that can communicate between the analyzer 800 and any component of the system 100.

The ultrasonic output drive lines 804 can provide a power source to the medical ablation instrument (e.g., the medical ablation instrument 102 of the system 100 from FIG. 1). The ultrasonic output drive lines 804 can provide ultrasonic, laser, or any other power that can be used by the medical ablation instrument 102 for the ablation of the target anatomical structure.

The white light source output fiber optic cables 806 can provide a white light to the system 100. The white light provided by the white light source output fiber optic cables 806 can provide the light that reflects, refracts, or interacts with the fragments of the target, and can be captured by the spectrometer.

The spectrometer input cables 808 capture the light from the white light source output fiber optic cables 806 after it has engaged with the fragments of the target in, for example, the measurement location (e.g., the measurement location 116 (FIG. 1) or the measurement chamber 250 (FIG. 2)). The spectrometer input cables 808 transmit the captured light from the white light source output fiber optic cables 806 to the spectrometer 282.

As discussed above, the spectral response 706 can be transmitted to the feature extractor 708 to prepare the spectral response 706 for analysis by the machine learning classifier 712. In response to the stone identification output 716 generated by the machine learning classifier 712, the analyzer 800 can adjust one or more parameters sent to the system 100 via the transducer cable 802. Specifically, the analyzer 800 can adjust one or more parameters of the ultrasonic output drive lines 804, which can adjust the ablation parameters of the medical ablation instrument 102. Adjusting the ablation parameters of the medical ablation instrument 102 can help expedite the ablation process and improve the ablation to obtain more predictable fragments of the target anatomical structure.

The target composition analyzer 800 can similarly perform any of the tasks or operations, as discussed regarding the target composition analyzer 700, with reference to FIG. 7.

Figure 9:
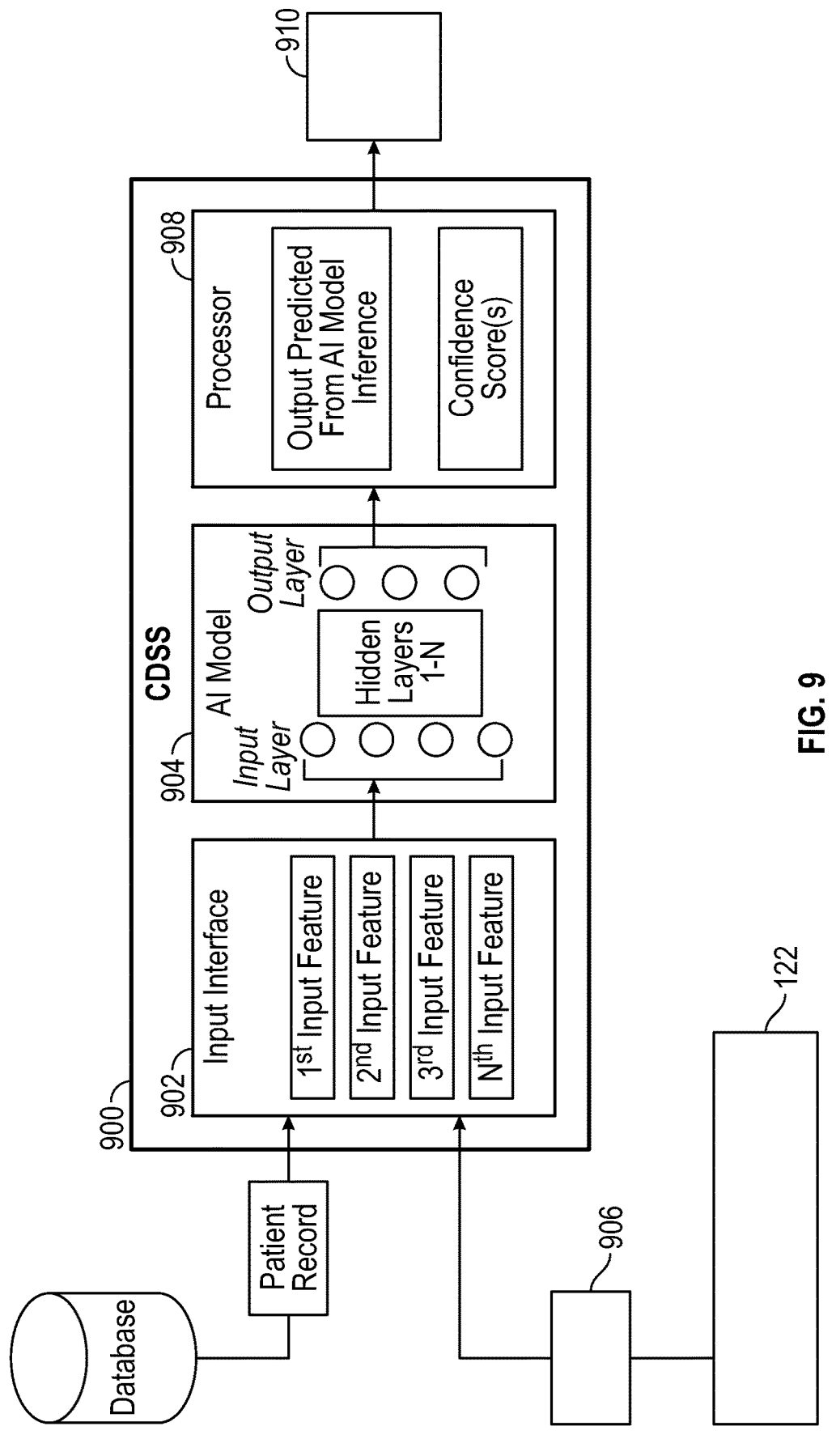
FIG. 9 is a schematic diagram of an example of a computer-based clinical decision support system configured to determine a composition of a target ablated from an anatomical site.

FIG. 9 is a schematic diagram of an example of a computer-based clinical decision support system (CDSS) 900 configured to determine a composition of a target ablated from an anatomical site. The CDSS 900 can include an input interface 902, an artificial intelligence (AI) model 904, and a processor 908. The input interface 902 can receive measurements 906 of the target 104 made by the spectrometer 282 (FIG. 2), which are specific to a patient, as input features. The input interface 902 can provide the input features to the AI model 904, where, in conjunction with processor 908, an output describing a type of kidney stone associated with the target 104 is generated. For example, an inference operation in which the measurements 906 of the target 104 made by the spectrometer 282 are applied to the AI model to generate the output describing a type of kidney stone associated with the target 104. The type of kidney stone can be calcium oxalate monohydrate, cystine, uric acid, and the like. the CDSS 900 can output a user interface (UI) 910 through which a type of kidney stone associated with the target 104 can be communicated to a user, e.g., a clinician.

The input interface 902 can be a direct data link between the CDSS 900 and one or more medical devices that generate at least some of the input features, such as the spectrometer 282. For example, the input interface 902 can transmit the measurements 906 of the target 104 made by the spectrometer 282 directly to the CDSS 900 during a therapeutic and/or diagnostic medical procedure. Additionally, or alternatively, the input interface 902 can be a classical user interface that facilitates interaction between a user and the CDSS 900. For example, the input interface 902 can facilitate a user interface through which the user may manually enter the measurements 906 of the target 104 made by the spectrometer 282. Additionally, or alternatively, the input interface 902 can provide the CDSS 900 with access to an electronic patient record from which one or more input features may be extracted. In any of these cases, the input interface 902 is configured to collect one or more input features in association with a specific patient on or before a time at which the CDSS 900 is used to assess the measurements 906 of the target 104 made by the spectrometer 282. The measurements 906 of the target 104 made by the spectrometer 282 can be provided to the input interface 902 as a first input feature through a $n^{th}$ input feature where there can be first through $n^{th}$ measurements associated with the measurements 906, as shown with reference to FIG. 9.

Based on one or more of the above input features, the processor 908 performs an inference operation using the AI model to generate an output describing a type of kidney stone associated with the target 104. For example, input interface 902 may deliver the first input feature through the $n^{th}$ input feature into an input layer of the AI model which propagates these input features through the AI model to an output layer. The AI model can provide a computer system the ability to perform tasks, without explicitly being programmed, by making inferences based on patterns found in data analysis. AI model can explore the study and construction of algorithms (e.g., machine-learning algorithms) that may learn from existing data and make predictions about new data. Such algorithms can build an AI model from example training data to make data-driven predictions or decisions expressed as outputs or assessments.

Modes for machine learning (ML) can include supervised ML and unsupervised ML. Supervised ML uses prior knowledge (e.g., examples that correlate inputs to outputs or outcomes) to learn the relationships between the inputs and the outputs. The goal of supervised ML is to learn a function that, given some training data, best approximates the relationship between the training inputs and outputs so that the ML model can implement the same relationships when given inputs to generate the corresponding outputs. Unsupervised ML is the training of an ML algorithm using information that is neither classified nor labeled and allowing the algorithm to act on that information without guidance. Unsupervised ML is useful in exploratory analysis because it can automatically identify structure in data.

Some suitable tasks for supervised ML are classification problems and regression problems. Classification problems, also referred to as categorization problems, aim at classifying items into one of several category values (for example, a determination of whether an object is an apple or an orange). Regression algorithms aim at quantifying some items (for example, by providing a score to the value of some input). Some examples supervised ML algorithms are Logistic Regression (LR), Naive-Bayes, Random Forest (RF), neural networks (NN), deep neural networks (DNN), matrix factorization, and Support Vector Machines (SVM).

Some suitable tasks for unsupervised ML include clustering, representation learning, and density estimation. Some examples unsupervised-ML algorithms are K-means clustering, principal component analysis, and autoencoders.

Another type of ML is federated learning (also referred to as collaborative learning) which can train an algorithm across multiple decentralized devices holding local data, without exchanging the data. This approach stands in contrast to centralized machine-learning techniques, in which all the local datasets are uploaded to one server, as well as to more classical decentralized approaches, which can assume that local data samples are identically distributed. Federated learning can enable multiple actors to build a shareable, robust machine learning model without sharing data, thus allowing it to address critical issues such as data privacy, data security, data access rights, and access to heterogeneous data.

The AI model may be trained continuously or periodically before the performance of the inference operation by the processor 908. Then, during the inference operation, the patient-specific input features provided to the AI model may be propagated from an input layer through one or more hidden layers and ultimately to an output layer corresponding to the type of kidney stone associated with the target 104. For example, when the output layer generates an output corresponding to a type of kidney stone associated with the target 104, a user, such as a clinician, can determine what type of ablation technique can be used to ablate the kidney stones. Specifically, based on the output relating to a type of kidney stone associated with the target 104 received from the CDSS 900, a user can select an efficient ablation technique. Moreover, the output corresponding to a type of kidney stone associated with the target 104 can be provided in real-time while the spectrometer 282 is taking measurements via the measurement location 116 such that ablation of the kidney stones can occur in real-time.

During and/or after the inference operation, the output relating to a type of kidney stone associated with the target 104 can be communicated to the user via the UI 910 or automatically cause display in communication with the processor 908 for performing a desired action. For example, the CDSS 900 can provide an audible output relating to the type of kidney stone associated with the target 104 or visual output relating to the type of kidney stone associated with the target 104. Either way, the output provides a quick method of informing a user of the type of kidney stone to allow the user to use the most appropriate ablation technique.

Figure 10:
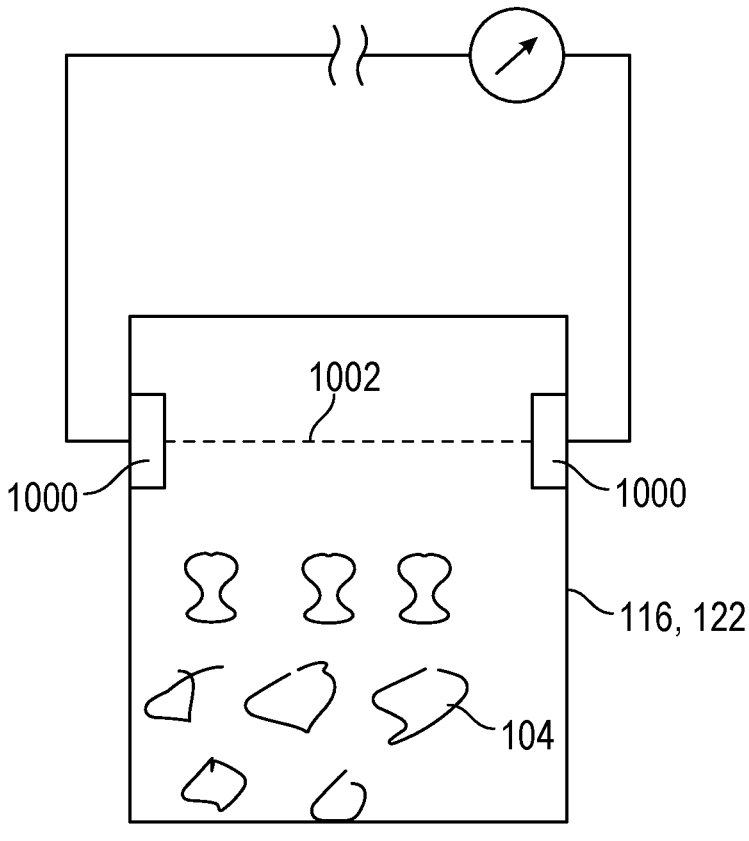
FIG. 10 illustrates an example sensor configuration for a system for analyzing ablated targets from an anatomical site.

FIG. 10 illustrates an example sensor configuration for a system for analyzing targets from an anatomical site. The measurement location 116 or removable trap filter 122 can include sensors 1000. The sensors 1000 can be used to detect when the target 104 within the removable trap filter 122 reaches the level 1002. In another example, the sensors 1000 can be used to analyze the fragments of the target 104, for example, similar to light source 280 and the spectrometer 282.

As shown in FIG. 10, the sensors 1000 can be used to determine when the fragments of the target 104 are at, or exceed the level 1002. Such examples of the sensors 1000 can be capacitors, optical, vision, acoustic, or any other type of sensor that can determine when the fragments of the target 104 reach the level 1002. When the sensors 1000 detect that the sensor 1000 fragments of the target 104 are at, or exceed, the level 1002 the sensors 1000 can transmit a signal. In response to the signal from the sensor 1000, there can be an alert, signal, or other indicator to indicate that the fragments of the target 104 are at or above level 1002. The signal can indicate to a user of the system 100 that the removable trap filter 122 should be emptied. A first of the sensor 1000 and a second of the sensors 1000 can be a receiver such that the transmitter can transmit a signal to the receiver along the level 1002. When the fragments of the target 104 exceed the level 1002, the fragments of the target 104 can interfere with the signal transmitted between the sensors 1000, thereby causing initiation of the signal.

The sensors 1000 can be used to analyze the fragments of the target 104 to determine a target composition characteristic of one or more fragments of the target 104. When the sensors 1000 are used to analyze the fragments of the target 104, the sensors 1000 can be located anywhere along the evacuation path 114. For example, the sensors 1000 can be installed within the measurement location 116, the removable trap filter 122, or any other location that the fragments of the target 104 travel therethrough. The sensors 1000 can be capacitors, optical, vision, acoustic, or any other type of sensor that can be used to analyze the fragments of the target 104. For example, the sensors 1000 can include an acoustic wave generator to produce an acoustic wave that propagates to the fragments of the target 104 within the evacuation path 114, the measurement location 116, or the removable trap filter 122. The sensors 1000 can also include an impedance sensor to generate an impedance-indicating signal from a change in amplitude and phase of the acoustic wave after the acoustic wave engages with the fragments of the target 104. Here, one or more of the controllers of the system (e.g., the controller 146 of the system 100) can be configured to determine at least one target composition characteristic of at least a portion of the ablated target based at least in part on the impedance-indicating signal. The controller can complete the analysis similar to the controllers that receive the spectral response 706 (FIG. 7) from the spectrometer 282.

In yet another example, the sensors 1000 can include one or more image sensors configured to capture an image of the fragments of the target 104. One or more of the controllers of the system 100 can compare the image captured by the sensors 1000 to reference images to determine at least one characterization of the fragments of the target 104.

FIG. 11 is a flowchart that describes a method 1100. The method 1100 can be for identifying, characterizing, or analyzing a target (e.g., the target 104 FIG. 1), or fragments of the target, to improve the ablation process of the target. The method 1100 can include operations 1110-1140.

At operation 1110, the method 1100 can include removing the at least a portion of the ablated target from an anatomic site along an evacuation path (e.g., the evacuation path 114 (FIG. 1)). A medical ablation instrument (e.g., the medical ablation instrument 102 (FIG. 1) can be used to remove at least a portion of a target from an anatomic site. The evacuation path can be configured to remove the ablated portion of the target from the patient. Thus, the evacuation path can be connected to a suction source (e.g., a wall vacuum at a hospital). As discussed herein, the evacuation path can include a measurement location (e.g., the measurement location 116 (FIG. 1)).

At operation 1120, the method 1100 can include generating turbulence at the measurement location. The turbulence can be generated using a turbulator (e.g., the turbulator 120). As discussed herein, the turbulator can be a static turbulator that agitates the mixture of liquid and the fragments of the target, as they travel through the evacuation path, or the turbulator can be a mechanical, hydraulic, pneumatic, or the like, turbulator that operates to agitate the liquid and the fragments of the target within the measurement site.

At operation 1130, the method 1100 can include determining, using a target-composition characterization system, a characteristic of the at least a portion of the ablated target at the measurement location when turbulence can be present at the measurement location.

For example, operation 1130 of the method 1100 can include receiving, with the controller circuitry, one or more signals from a spectrometer, analyzing the one or more signals to determine the target composition characteristic of the at least a portion of the ablated target, and comparing the target composition characteristic of the at least a portion of the ablated target to at least one criterion. The method 1100 can also include generating an output indicative of the target identification based on the comparison.

For example, operation 1130 of the method 1100 can include receiving, with the controller circuitry, one or more signals from an impedance sensor, which can be indicative of the effects of the fragments of the target on an acoustic wave as the wave propagates through the measurement location. The sensors can generate an impedance signal using a sensor for sensing a change in amplitude and phase of the acoustic wave passing the measurement location. The operation 1130 of the method 1100 can also include determining, using controller circuitry, the target composition characteristic of the at least one portion of the ablated target based at least in part on the impedance signal.

At operation 1140, the method 1100 can include adjusting, using controller circuitry, an ablation parameter based at least in part on the determined target composition characteristic of the at least a portion of the ablated target. The ablation parameter can be power provided to the ablation instrument, a mode of the ablation instrument, or a suggested type of the ablation instrument, or the like. As discussed herein, the controller can also send a signal indicative of the identified fragments of the target, which can alter the behavior of any of the components of the system.

Figure 12:
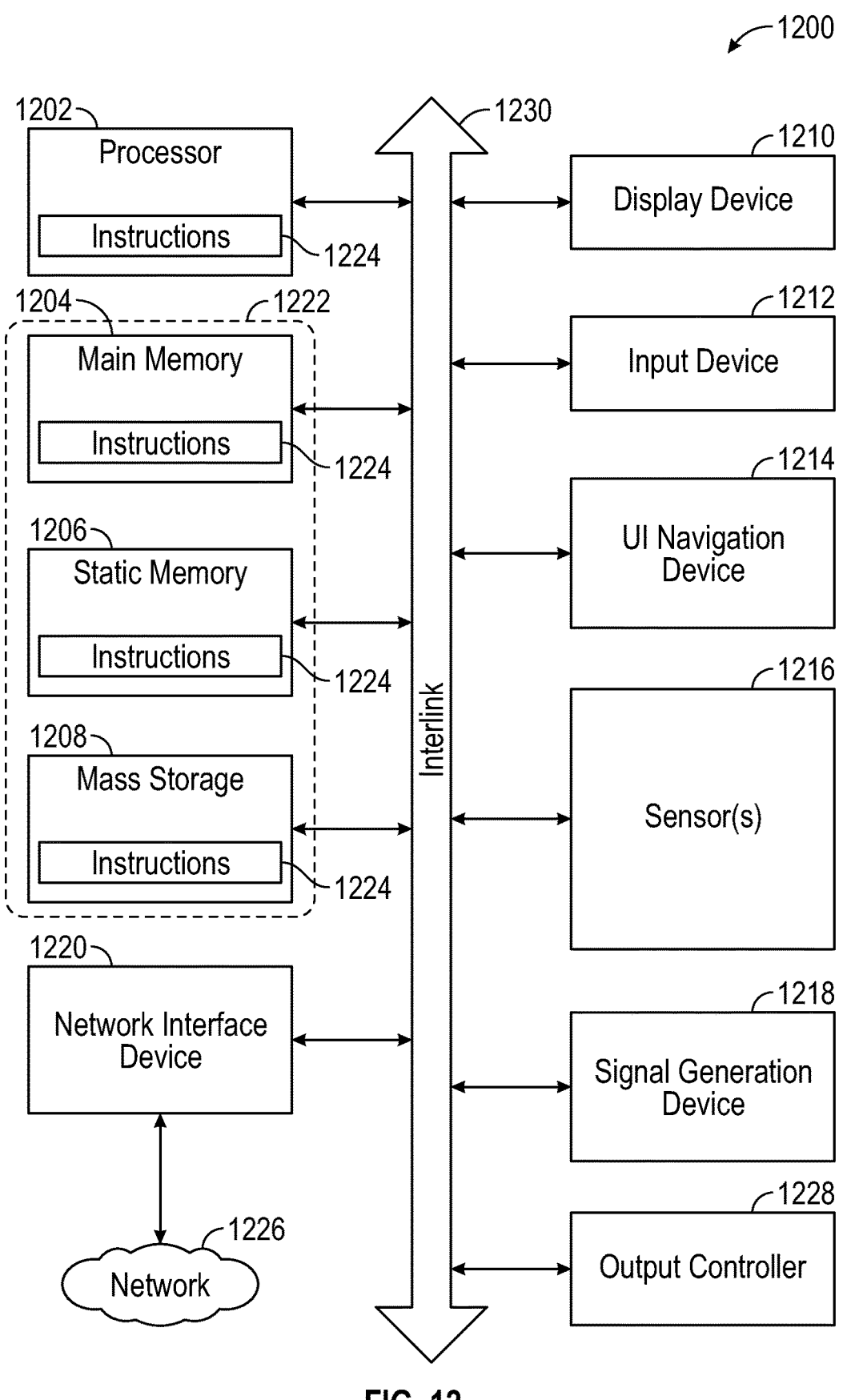
FIG. 12 is a block diagram illustrating an example of a machine upon which one or more examples may be implemented.

FIG. 12 illustrates a block diagram of an example machine 1200 upon which any one or more of the techniques (e.g., methodologies) discussed herein may perform. Examples, as described herein, may include, or may operate by, logic or a number of components, or mechanisms in the machine 1200. Circuitry (e.g., processing circuitry) is a collection of circuits implemented in tangible entities of the machine 1200 that include hardware (e.g., simple circuits, gates, logic, etc.). Circuitry membership may be flexible over time. Circuitries include members that may, alone or in combination, perform specified operations when operating. Hardware of the circuitry may be immutably designed to carry out a specific operation (e.g., hardwired). The hardware of the circuitry may include variably connected physical components (e.g., execution units, transistors, simple circuits, etc.) including a machine readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuitry in hardware via the variable connections to carry out portions of the specific operation when in operation. Accordingly, the machine-readable medium elements are part of the circuitry or are communicatively coupled to the other components of the circuitry when the device is operating. In an example, any of the physical components may be used in more than one member of more than one circuitry. For example, under operation, execution units may be used in a first circuit of a first circuitry at one point in time and reused by a second circuit in the first circuitry, or by a third circuit in a second circuitry at a different time. Additional examples of these components with respect to the machine 1200 follow.

The machine 1200 may operate as a standalone device or may be connected (e.g., networked) to other machines. In a networked deployment, the machine 1200 may operate in the capacity of a server machine, a client machine, or both in server-client network environments. The machine 1200 may act as a peer machine in peer-to-peer (P2P) (or other distributed) network environment. The machine 1200 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, the term "machine" includes any collection of machines that individually or jointly execute a set (or multiple sets) of instructions to perform any one or more of the methodologies discussed herein, such as cloud computing, software as a service (SaaS), other computer cluster configurations.

The machine (e.g., computer system) 1200 may include a hardware processor 1202 (e.g., a central processing unit (CPU), a graphics processing unit (GPU), a hardware processor core, or any combination thereof), a main memory 1204, a static memory (e.g., memory or storage for firmware, microcode, a basic-input-output (BIOS), unified extensible firmware interface (UEFI), etc.) 1206, and mass storage 1208 (e.g., hard drives, tape drives, flash storage, or other block devices) some or all of which may communicate with each other via an interlink (e.g., bus) 1230. The machine 1200 may further include a display unit 1210, an alphanumeric input device 1212 (e.g., a keyboard), and a user interface (UI) navigation device 1214 (e.g., a mouse). The display unit 1210, input device 1212 and UI navigation device 1214 may be a touch screen display. The machine 1200 may additionally include a storage device (e.g., drive unit) 1208, a signal generation device 1218 (e.g., a speaker), a network interface device 1220, and one or more sensors 1216, such as a global positioning system (GPS) sensor, compass, accelerometer, or other sensor. The machine 1200 may include an output controller 1228, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

Registers of the processor 1202, the main memory 1204, the static memory 1206, or the mass storage 1208 may be, or include, a machine readable medium 1222 on which is stored one or more sets of data structures or instructions 1224 (e.g., software) embodying or utilized by any one or more of the techniques or functions described herein. The instructions 1224 may also reside, completely or at least partially, within any of registers of the processor 1202, the main memory 1204, the static memory 1206, or the mass storage 1208 during execution thereof by the machine 1200. In an example, one or any combination of the hardware processor 1202, the main memory 1204, the static memory 1206, or the mass storage 1208 may constitute the machine readable media 1222. While the machine readable medium 1222 is illustrated as a single medium, the term "machine readable medium" may include a single medium or multiple media (e.g., a centralized or distributed database, and/or associated caches and servers) configured to store the one or more instructions 1224.

The term "machine readable medium" may include any medium that is capable of storing, encoding, or carrying instructions for execution by the machine 1200 and that cause the machine 1200 to perform any one or more of the techniques of the present disclosure, or that is capable of storing, encoding or carrying data structures used by or associated with such instructions. Non-limiting machine readable medium examples may include solid-state memories, optical media, magnetic media, and signals (e.g., radio frequency signals, other photon based signals, sound signals, etc.). In an example, a non-transitory machine readable medium comprises a machine readable medium with a plurality of particles having invariant (e.g., rest) mass, and thus are compositions of matter. Accordingly, non-transitory machine-readable media are machine readable media that do not include transitory propagating signals. Specific examples of non-transitory machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

Information stored or otherwise provided on the machine readable medium 1222 may be representative of the instructions 1224, such as instructions 1224 themselves or a format from which the instructions 1224 may be derived. This format from which the instructions 1224 may be derived may include source code, encoded instructions (e.g., in compressed or encrypted form), packaged instructions (e.g., split into multiple packages), or the like. The information representative of the instructions 1224 in the machine readable medium 1222 may be processed by processing circuitry into the instructions to implement any of the operations discussed herein. For example, deriving the instructions 1224 from the information (e.g., processing by the processing circuitry) may include: compiling (e.g., from source code, object code, etc.), interpreting, loading, organizing (e.g., dynamically or statically linking), encoding, decoding, encrypting, unencrypting, packaging, unpackaging, or otherwise manipulating the information into the instructions 1224.

The derivation of the instructions 1224 may include assembly, compilation, or interpretation of the information (e.g., by the processing circuitry) to create the instructions 1224 from some intermediate or preprocessed format provided by the machine readable medium 1222. The information, when provided in multiple parts, may be combined, unpacked, and modified to create the instructions 1224. For example, the information may be in multiple compressed source code packages (or object code, or binary executable code, etc.) on one or several remote servers. The source code packages may be encrypted when in transit over a network and decrypted, uncompressed, assembled (e.g., linked) if necessary, and compiled or interpreted (e.g., into a library, stand-alone executable etc.) at a local machine, and executed by the local machine.

The instructions 1224 may be further transmitted or received over a communications network 1226 using a transmission medium via the network interface device 1220 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), LoRa/LoRaWAN, or satellite communication networks, mobile telephone networks (e.g., cellular networks such as those complying with 3G, 4G LTE/LTE-A, or 5G standards), Plain Old Telephone (POTS) networks, and wireless data networks (e.g., Institute of Electrical and Electronics Engineers (IEEE) 802.11 family of standards known as Wi-Fi®, IEEE 802.15.4 family of standards, peer-to-peer (P2P) networks, among others. The network interface device 1220 may include one or more physical jacks (e.g., Ethernet, coaxial, or phone jacks) or one or more antennas to connect to the communications network 1226. The network interface device 1220 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any medium that is capable of storing, encoding or carrying instructions for execution by the machine 1200, and includes digital or analog communications signals or other medium to facilitate communication of such software. A transmission medium is a machine-readable medium.

The following examples detail certain aspects of the present subject matter to solve the challenges and provide the benefits discussed herein, among others.

Example 1 is a system that can include a medical target ablation instrument for ablating a target located at an anatomic site within a patient, the ablation instrument defining therewithin an evacuation path for transporting the ablated target away from the anatomic site; a turbulator for generating turbulence at a measurement location along the evacuation path; and a target composition characterization system, operatively coupled to the measurement location along the evacuation path for determining a composition characteristic of at least a portion of the ablated target along the evacuation path within the ablation instrument.

In Example 2, the subject matter of Example 1 can include, wherein the evacuation path further comprises: a receptacle located downstream of the measurement location for storing the ablated target.

In Example 3, the subject matter of Example 2 can include, wherein the measurement location comprises a measurement chamber that comprises: an inlet valve to direct the ablated target into the measurement chamber; and an outlet valve to direct the ablated target out of the measurement chamber.

In Example 4, the subject matter of Example 3 can include, wherein the evacuation path comprises: a bypass valve to direct the ablated target around the measurement chamber and directly into the receptacle.

In Example 5, the subject matter of Example 4 can include, wherein the system includes controller circuitry that is configured to operate in a plurality of modes, the plurality of modes including a sample measurement mode and a sample trap mode.

In Example 6, the subject matter of Example 5 can include, wherein in the sample measurement mode, the controller circuitry actuates the inlet valve to be open, the outlet valve to be closed, and the bypass valve to be closed, and wherein in the sample trap mode, the controller circuitry actuates the inlet valve to be closed, the outlet valve to be open, and the bypass valve to be open.

In Example 7, the subject matter of Examples 1-6 can include, controller circuitry for adjusting a parameter associated with the medical target ablation instrument based at least in part on the determined characteristic of the at least a portion of the ablated target.

In Example 8, the subject matter of Example 7 can include, wherein the controller circuitry is coupled to memory circuitry including stored instructions that, when performed by the controller circuitry, cause the controller circuitry to: receive an inflow rate indicative of a fluid flow going into a measurement chamber along the evacuation path; receive an outflow rate indicative of a fluid flow leaving the measurement chamber; and establish or adjust the inflow rate or the outflow rate to at least one of establish, adjust, or maintain a target turbulence level using the turbulator.

In Example 9, the subject matter of Examples 7-8 can include, wherein the target composition characterization system comprises: a light source for illuminating the ablated target at the measurement location; and a spectrometer for detecting a response signal from at least a portion of the ablated target in response to the illumination; wherein the controller circuitry determines the composition characteristic of the at least a portion of the ablated target based on at least in part on the detected response signal.

In Example 10, the subject matter of Example 9 can include, wherein the controller circuitry is coupled to memory circuitry including instructions that, when performed by the controller circuitry, cause the controller circuitry to: receive the response signal from the spectrometer; analyze the response signal to determine the composition characteristic of the at least a portion of the ablated target; compare the composition characteristic of the at least a portion of the ablated target to at least one criterion; and generate an output based on the comparison.

In Example 11, the subject matter of Example 10 can include, a convolutional neural network connected to the controller circuitry, wherein the controller circuitry is configured to: transmit a signal from the spectrometer to the convolutional neural network; transmit the output indicative of the target composition characteristic to the convolutional neural network; and receive one or more updated instructions, based on an output of the convolutional neural network.

In Example 12, the subject matter of Examples 7-11 can include, wherein the target composition characterization system comprises: an acoustic wave generator to produce an acoustic wave that propagates to the measurement location along the evacuation path; an impedance sensor to generate an impedance-indicating signal from a change in amplitude and phase of the acoustic wave after the acoustic wave has traveled through the measurement location; and the controller circuitry is configured for determining the target composition characteristic of the at least a portion of the ablated target based at least in part on the impedance-indicating signal.

In Example 13, the subject matter of Example 12 can include, wherein the controller circuitry is coupled to memory circuitry including instructions that, when performed by the controller circuitry, cause the controller circuitry to: receive the impedance-indicating signal from the impedance sensor; analyze the impedance-indicating signal to determine the target composition characteristic of the at least a portion of the ablated target; compare the target composition characteristic of the at least a portion of the ablated target to at least one reference characteristic; and generate an output indicative of an identity of the target based on the comparison.

In Example 14, the subject matter of Example 13 can include, a convolutional neural network connected to the controller circuitry, the controller circuitry configured to: transmit the impedance-indicating signal to the convolutional neural network; transmit the output indicative of the target composition characteristic to the convolutional neural network; and receive one or more updated acoustic impedance algorithms.

In Example 15, the subject matter of Examples 1-14 can include, a particle sensor, arranged for measuring a quantity of particles within at least a portion of the evacuation path; and controller circuitry, coupled to the particle sensor, to calculate an ablation rate of the target based at least in part on the measured quantity of the particles.

In Example 16, the subject matter of Examples 7-15 can include, wherein the target composition characteristic system further comprises: an imaging device for imaging the ablated target along the evacuation path; and an object-detection system for detecting the ablated target in an image of the ablated target acquired by the imaging device, wherein the controller circuitry determines the target composition characteristic of the ablated target based at least in part on the image of the ablated target acquired by the imaging device.

In Example 17, the subject matter of Example 16 can include, wherein the target composition characterization system is trained to recognize a plurality of ablated target characteristics.

In Example 18, the subject matter of Examples 16-17 can include, wherein the controller circuitry is coupled to memory circuitry including instructions that, when performed by the controller circuitry, cause the controller circuitry to: receive an output from the object-detection system; analyze the output to determine the target composition characteristic of the at least a portion of the ablated target; compare the target composition characteristic of the at least a portion of the ablated target to at least one criterion; and generate an output indicative of an identity of the target based on the comparison.

In Example 19, the subject matter of Example 18 can include, a convolutional neural network connected to the controller circuitry, the controller circuitry configured to: transmit the output from the object-detection system to the convolutional neural network; transmit the output indicative of the target composition characteristic to the convolutional neural network; and receive one or more updated object-detection instructions based on an output of the convolutional neural network in response to the output from the object-detection system and in response to the output indicative of an identity of the target.

Example 20 is a method for identifying a target with a system, the system including a target-identification system for determining a target composition characteristic of at least a portion of an ablated target, the method comprising: removing the at least a portion of the ablated target from an anatomic site along an evacuation path, the evacuation path including: a measurement location; generating turbulence at the measurement location using a turbulator; determining, using a target-composition characterization system, a characteristic of the at least a portion of the ablated target at the measurement location when turbulence is present at the measurement location; and adjusting, using controller circuitry, an ablation parameter based at least in part on the determined target composition characteristic of the at least a portion of the ablated target.

In Example 21, the subject matter of Example 20 can include, receiving, with the controller circuitry, one or more signals from a spectrometer; analyzing the one or more signals to determine the target composition characteristic of the at least a portion of the ablated target; comparing the target composition characteristic of the at least a portion of the ablated target to at least one criterion; and generating an output indicative of the target identification based on the comparison.

In Example 22, the subject matter of Examples 20-21 can include, producing an acoustic wave that propagates to the measurement location; generating an impedance signal using a sensor for sensing a change in amplitude and phase of the acoustic wave passing the measurement location; and determining, using controller circuitry, the target composition characteristic of the at least one portion of the ablated target based at least in part on the impedance signal.

In Example 23, the subject matter of Example 22 can include, receiving, with the controller circuitry, the impedance signal; analyzing the impedance signal to determine the target composition characteristic of the at least a portion of the ablated target; comparing the target composition characteristic of the at least a portion of the ablated target to at least one criterion; and generating an output indicative of an identity of the target based on the comparison.

Example 24 is at least one machine-readable medium including instructions that, when executed by processing circuitry, cause the processing circuitry to perform operations to implement of any of Examples 1-23.

Example 25 is an apparatus comprising means to implement of any of Examples 1-23.

Example 26 is a system to implement of any of Examples 1-23.

Example 27 is a method to implement of any of Examples 1-23.

Example 28 is a system, method, or apparatus of any element of Examples 1-23.

The above-detailed description includes references to the accompanying drawings, which form a part of the detailed description. The drawings show, by way of illustration, specific embodiments that may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 10% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, 4.24, and 5). Similarly, numerical ranges recited herein by endpoints include subranges subsumed within that range (e.g. 1 to 5 includes 1-1.5, 1.5-2, 2-2.75, 2.75-3, 3-3.90, 3.90-4, 4-4.24, 4.24-5, 2-5, 3-5, 1-4, and 2-4). It is also to be understood that all numbers and fractions thereof are presumed to be modified by the term "about."

The above description is intended to be illustrative, and not restrictive. For example, the above-described examples (or one or more aspects thereof) may be used in combination with each other. Other examples may be used, such as by one of ordinary skill in the art upon reviewing the above description. The Abstract is to allow the reader to quickly ascertain the nature of the technical disclosure and is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the examples should be determined with reference to the appended claims, along with the full scope of equivalents to which such claims are entitled.

The invention claimed is:

1. A system comprising:
   a medical target ablation instrument for ablating a target located at an anatomic site within a patient, the medical target ablation instrument defining therewithin an evacuation path for transporting the ablated target away from the anatomic site;
   a measurement chamber located along the evacuation path;
   a turbulator configured to generate turbulence within the measurement chamber; and
   a target composition characterization system, operatively coupled to the measurement chamber, the target composition characterization system configured to determine a composition characteristic of the ablated target during agitation within the measurement chamber.

2. The system of claim 1, wherein the evacuation path further comprises:
   a receptacle located downstream of the measurement chamber for storing the ablated target.

3. The system of claim 2, wherein the measurement chamber comprises:

an inlet valve to direct the ablated target into the measurement chamber; and an outlet valve to direct the ablated target out of the measurement chamber.

4. The system of claim 3, wherein the evacuation path comprises:

a bypass valve to direct the ablated target around the measurement chamber and directly into the receptacle.

5. The system of claim 4, wherein the system includes controller circuitry that is configured to operate in a plurality of modes, the plurality of modes including a sample measurement mode and a sample trap mode.

6. The system of claim 5, wherein in the sample measurement mode, the controller circuitry actuates the inlet valve to be open, the outlet valve to be closed, and the bypass valve to be closed, and wherein in the sample trap mode, the controller circuitry actuates the inlet valve to be closed, the outlet valve to be open, and the bypass valve to be open.

7. The system of claim 1, further comprising:

controller circuitry for adjusting a parameter associated with the medical target ablation instrument based at least in part on the determined composition characteristic of at least a portion of the ablated target.

8. The system of claim 7, wherein the controller circuitry is coupled to memory circuitry including stored instructions that, when performed by the controller circuitry, cause the controller circuitry to:

receive an inflow rate indicative of a fluid flow going into the measurement chamber;

receive an outflow rate indicative of a fluid flow leaving the measurement chamber; and establish or adjust the inflow rate or the outflow rate to at least one of establish, adjust, or maintain a target turbulence level using the turbulator.

9. The system of claim 7, wherein the target composition characterization system comprises:

a light source for illuminating the ablated target within the measurement chamber; and a spectrometer for detecting a response signal from the at least a portion of the ablated target in response to the illumination;

wherein the controller circuitry determines the composition characteristic of the at least a portion of the ablated target based on at least in part on the detected response signal.

10. The system of claim 9, wherein the controller circuitry is coupled to memory circuitry including instructions that, when performed by the controller circuitry, cause the controller circuitry to:

receive the response signal from the spectrometer;

analyze the response signal to determine the composition characteristic of the at least a portion of the ablated target;

compare the composition characteristic of the at least a portion of the ablated target to at least one criterion; and generate an output based on the comparison.

11. The system of claim 10, comprising:

a convolutional neural network connected to the controller circuitry, wherein the controller circuitry is configured to:

transmit a signal from the spectrometer to the convolutional neural network;

transmit the output indicative of the target composition characteristic to the convolutional neural network; and receive one or more updated instructions, based on an output of the convolutional neural network.

12. The system of claim 7, wherein the target composition characterization system comprises:

an acoustic wave generator to produce an acoustic wave that propagates to the measurement location along the evacuation path;

an impedance sensor to generate an impedance-indicating signal from a change in amplitude and phase of the acoustic wave after the acoustic wave has traveled through the measurement location; and the controller circuitry is configured for determining the target composition characteristic of the at least a portion of the ablated target based at least in part on the impedance-indicating signal.

13. The system of claim 12, wherein the controller circuitry is coupled to memory circuitry including instructions that, when performed by the controller circuitry, cause the controller circuitry to:

receive the impedance-indicating signal from the impedance sensor;

analyze the impedance-indicating signal to determine the target composition characteristic of the at least a portion of the ablated target;

compare the target composition characteristic of the at least a portion of the ablated target to at least one reference characteristic; and generate an output indicative of an identity of the target based on the comparison.

14. The system of claim 13, comprising:

a convolutional neural network connected to the controller circuitry, the controller circuitry configured to:

transmit the impedance-indicating signal to the convolutional neural network;

transmit the output indicative of the target composition characteristic to the convolutional neural network; and receive one or more updated acoustic impedance algorithms.

15. The system of claim 7, wherein the target composition characteristic system further comprises:

an imaging device for imaging the ablated target along the evacuation path; and an object-detection system for detecting the ablated target in an image of the ablated target acquired by the imaging device, wherein the controller circuitry determines the target composition characteristic of the ablated target based at least in part on the image of the ablated target acquired by the imaging device.

16. The system of claim 15, wherein the target composition characterization system is trained to recognize a plurality of ablated target characteristics.

17. The system of claim 15, wherein the controller circuitry is coupled to memory circuitry including instructions that, when performed by the controller circuitry, cause the controller circuitry to:

receive an output from the object-detection system;

analyze the output to determine the target composition characteristic of the at least a portion of the ablated target;

compare the target composition characteristic of the at least a portion of the ablated target to at least one criterion; and generate an output indicative of an identity of the target based on the comparison.

18. The system of claim 17, comprising:

a convolutional neural network connected to the controller circuitry, the controller circuitry configured to:

transmit the output from the object-detection system to the convolutional neural network;

transmit the output indicative of the target composition characteristic to the convolutional neural network; and receive one or more updated object-detection instructions based on an output of the convolutional neural network in response to the output from the object-detection system and in response to the output indicative of an identity of the target.

19. The system of claim 1, comprising:

a particle sensor, arranged for measuring a quantity of particles within at least a portion of the evacuation path; and controller circuitry, coupled to the particle sensor, to calculate an ablation rate of the target based at least in part on the measured quantity of the particles.

20. The system of claim 1, wherein the turbulator is located at least partially within the measurement chamber.

21. The system of claim 1, wherein the measurement chamber includes a first cross-sectional area and the evacuation path defines a second cross-sectional area, and wherein the first cross-sectional area is greater than the second cross-sectional area.

\*  \*  \*  \*  \*